(12) United States Patent
Aschwanden et al.

(10) Patent No.: US 10,371,870 B2
(45) Date of Patent: Aug. 6, 2019

(54) VARIABLE FOCUS LENS

(71) Applicant: Optotune AG, Dietikon (CH)

(72) Inventors: Manuel Aschwanden, Allenwinden (CH); David Niederer, Kuttigen (CH); Philipp Waibel, Zurich (CH)

(73) Assignee: OPTOTUNE AG, Dietikon (CH)

( * ) Notice: Subject to any disclaimer, the term of this patent is extended or adjusted under 35 U.S.C. 154(b) by 0 days.

(21) Appl. No.: 15/561,054

(22) PCT Filed: Mar. 24, 2016

(86) PCT No.: PCT/EP2016/056680
§ 371 (c)(1),
(2) Date: Sep. 24, 2017

(87) PCT Pub. No.: WO2016/151123
PCT Pub. Date: Sep. 29, 2016

(65) Prior Publication Data
US 2018/0074233 A1 Mar. 15, 2018

(51) Int. Cl.
| | |
|---|---|
| *G02B 3/14* | (2006.01) |
| *G02B 7/10* | (2006.01) |
| *G02B 7/182* | (2006.01) |
| *G02B 26/00* | (2006.01) |
| *A61B 1/00* | (2006.01) |
| *G02C 7/08* | (2006.01) |

(52) U.S. Cl.
CPC ............... *G02B 3/14* (2013.01); *G02B 7/10* (2013.01); *G02B 7/182* (2013.01); *G02B 26/005* (2013.01); *A61B 1/0019* (2013.01); *G02C 7/085* (2013.01)

(58) Field of Classification Search
CPC ... G02B 3/14; G02B 3/12; G02B 7/10; G02B 7/182; G02B 26/005; G02C 7/085; A61B 1/0019
USPC .................................................. 359/665, 666
See application file for complete search history.

(56) References Cited

U.S. PATENT DOCUMENTS

| | | | |
|---|---|---|---|
| 3,432,218 A | 3/1969 | Loughridge et al. | |
| 3,830,021 A * | 8/1974 | Blum | B24B 13/005 451/390 |
| 3,913,061 A * | 10/1975 | Green | G02B 7/1805 181/176 |
| 5,028,833 A | 7/1991 | Kawai | |
| 8,390,724 B2 * | 3/2013 | Toyomura | H04N 7/185 348/335 |
| 2002/0044347 A1 * | 4/2002 | Steenblik | G02B 21/0008 359/368 |
| 2008/0170845 A1 * | 7/2008 | Kurosawa | G03B 13/34 396/133 |
| 2010/0232161 A1 | 9/2010 | Aschwanden et al. | |
| 2010/0277295 A1 * | 11/2010 | Matthews | F21L 4/005 340/332 |
| 2011/0007161 A1 | 1/2011 | Batchko et al. | |
| 2012/0069165 A1 * | 3/2012 | Choi | H04N 1/00413 348/61 |

* cited by examiner

*Primary Examiner* — William R Alexander
(74) *Attorney, Agent, or Firm* — JMB Davis Ben-David

(57) ABSTRACT

The invention relates to a variable focus lens comprising an elastically deformable optical element (7) and a circumferential mechanism (10, 1, 5, 2, 3, 8, 21) to transfer a rotational movement to an axial movement, wherein by using a ball bearing system (9, 11, 12, 13, 15, 16, 17) the mechanism is optimized in a manner to reduce mechanical friction, friction variation and to improve force-direction dependent positioning insensitivity.

12 Claims, 6 Drawing Sheets

VARIABLE FOCUS LENS

CROSS-REFERENCE TO RELATED APPLICATIONS

This is the U.S. National Stage of International Application No. PCT/EP2016/056680 filed on Mar. 24, 2016, which was published in English under PCT Article 21(2), which in turn claims priority to U.S. Provisional Patent Application No. 62/137,280 filed on Mar. 24, 2015.

TECHNICAL FIELD

The invention relates to a precise mechanically tunable adaptive fluid or liquid lens, with improved mechanical characteristics, namely with reduced mechanical friction and torque effects during tuning procedures and reduced mechanical play for improvements in optical repeatability and accuracy.

The use of the lens according to the invention is very versatile and further includes without limitation devices such as: vision systems, ophthalmic lenses, ophthalmology equipment such as phoropter, refractometer, fundus cameras, ppt. biometrie, perimeter, tonometer, anomaloscope, contrastometer, endothelmicroscope, anomaloscope, binoptometer, OCT, rodatest, ophthalmoscope, RTA, slitlamp microscope, surgical microscope, auto-refractometer, keratograph, confocal imager, Scheimpflug camera, wavefront aberrometer, pupillometer, skin laser, eye laser, otoscope, laryngoscope, Raman spectrometer, portable spectrometer, photodynamic diagnosis; as well as lighting devices, Lighting fixtures, devices for machine vision, laser processing devices, devices for conducting a light show, printers, metrology devices, (e.g. head-worn) glasses, medical devices, robot cams, motion tracking devices, microscopes, telescopes, endoscopes, binoculars, surveillance cameras, automotive devices, projectors, ophthalmic lenses, range finder, bar code readers, and web cams, fiber coupling, biometric devices, electronic magnifiers, motion tracking, intra-ocular lenses, mobile phones, military, digital still cameras, web cams, microscopes, telescopes, endoscopes, binoculars, research, industrial applications.

BACKGROUND ART

A lens of this basic functionality is shown in U.S. Pat. No. 8,000,022. The lens consists out of an inner, at least partially deformable optical lens container element which changes its shape upon applying a force to its deformable element. The force is created by an external actuator which can be an electronic actuator, such as electromotors or piezoactuators, but also thermal actuators, hydraulic actuators or an operator's hand or others. The force is transferred through a mechanical system which typically from a rotatory movement translates to a linear movement, typically perpendicular to the rotary movement. That linear movement is particularly used to move either a ring element or the lens container and transfers force to the elastic optical element. The applied force deforms the elastic element and the fluid or elastic lens body changes its optical properties, namely its focal length.

Based on the prior art, the problem underlying the present invention is to provide an improved variable focus lens.

This problem is solved by the lens according to claim 1. Preferred embodiments are stated in the sub claims and are further described below.

According to claim 1, a variable focus lens is disclosed (i.e. a lens that comprises an adjustable focal length) that comprises an elastically deformable optical element and a circumferential mechanism that is configured to transfer (or convert) a rotational movement to an axial movement in an axial direction, wherein said mechanism comprises a ball bearing system, particularly in order to reduce mechanical friction, friction variation, and particularly in order to improve force-direction dependent positioning insensitivity.

Further, according to an embodiment, the lens comprises an elastic element for preloading the ball bearing system.

Further, according to an embodiment, the lens comprises at least one ring-shaped elastic spring element configured to apply a preloading force in a primarily axial direction (or oriented along the axial direction) so as to avoid axial play within a helical thread, and optionally also to minimize optical hysteresis in the focal length behavior of the lens.

Further, according to an embodiment, said spring element is also configured to apply a preload in a rotational direction to reduce rotational play.

Further, according to an embodiment, the circumferential mechanism comprises an outer thread ring with a helical thread (e.g. facing inwards), which thread ring is supported on a fixed element via a ball bearing comprised by the ball bearing system so that the thread ring is rotatable with respect to the fixed element about the axial direction (e.g. optical axis of the lens).

Further, according to an embodiment, the lens comprises a container element. Further, the container element can comprise a container ring. Further, the container element can comprise said elastically deformable optical element or a transparent and elastically deformable membrane (which may form said elastically deformable optical element). Further, the container element can comprise a particularly transparent cover element facing said membrane in the axial direction. Further, the membrane, the container ring (forming e.g. a lateral circumferential wall of the container element) and the cover element can delimit a volume of the container element that is filled with a fluid. Further, the fluid can be transparent. Furthermore, the fluid may be a liquid or a gas, or may be a mixture of a liquid or a gas. Preferably, the fluid is a liquid, particularly a transparent liquid.

Further, instead of a lens, the mechanism of the present invention may also be applied to an adaptive mirror. Here, the container element may form a mirror that can be adapted (e.g. according to the principles described herein).

Further, according to an embodiment, the container element is guided by a plurality of posts protruding from the fixed element in the axial direction and extending through through holes formed in the container ring (and particularly also through through holes in said elastic spring element, see also below).

Further, according to an embodiment, the container ring comprises an outer thread (facing outwards) that engages with the helical thread so that the container element is moved axially in the axial direction when the thread ring is rotated about the axial direction, wherein a lens shaping element that protrudes from the fixed element is configured to press against the membrane depending on the axial position of the container element with respect to the fixed element/lens shaper so that a curvature of the membrane and therewith the focal length of the lens is adjustable by said axial movement of the container element.

Further, according to an embodiment, the container ring comprises a first ring and a second ring which both form said outer thread of the container ring, wherein said spring element is arranged between the first ring and the second ring and pushes the rings apart, so as to reduce an axial play of the helical thread, wherein particularly the spring element is configured to push said rings apart in a way that the axial contact to the thread ring is maintained always on the same side on the helical thread. The second ring may form a lock nut while the first ring may be fixed (or integrally connected) to a lateral circumferential wall of the container element to which the membrane and the cover element are fixed to enclose said volume of the container element in which the fluid or liquid resides. Preferably, each vertical post extends through associated through holes formed in the first and the second ring as well as in the annular spring element, wherein for each post the respective through holes are arranged on top of each other in the axial direction.

Further, according to an embodiment, the thread ring is also supported on a housing part that faces the fixed element in the axial direction via a further ball bearing (i.e. in the axial direction the thread ring is arranged between the two ball bearings) comprised by said ball bearing system, wherein said housing part particularly holds a further particularly transparent cover element facing said transparent cover element of the container element in the axial direction, and wherein particularly said housing part is connected to the vertical posts via an elastic bearing that may comprise flexure bearings or helical tension springs. Further, the two cover elements can be made out of a glass.

In the following, further advantages, features, embodiments and aspects of the present invention are described with reference to the Figures, wherein.

Figure 1A:
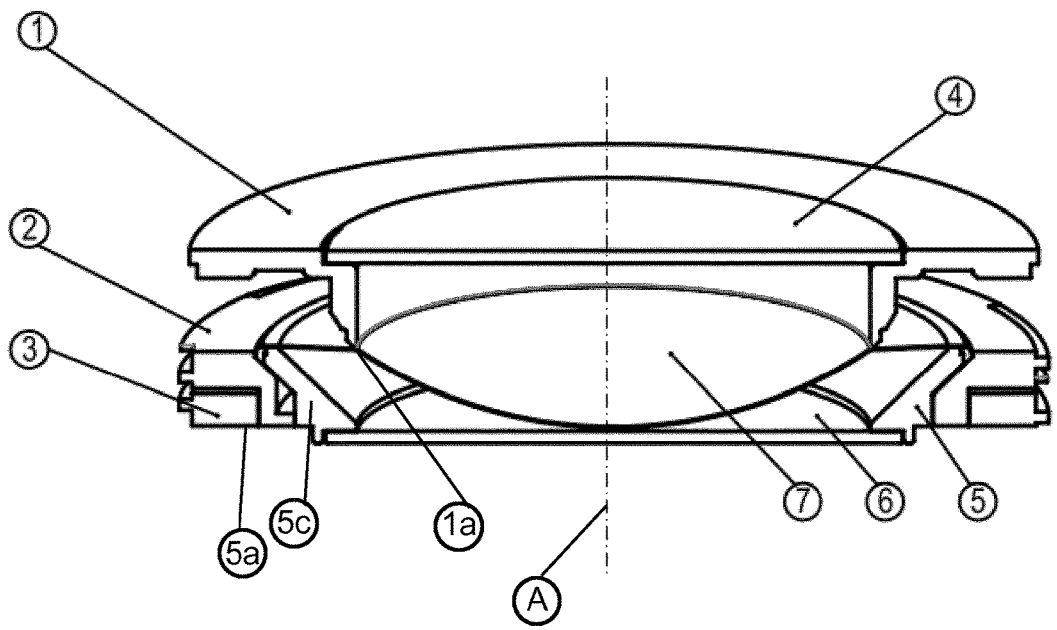
FIG. 1A, 1B show cross sectional views of a container and fixed element of a first embodiment of the focus variable lens according to the invention, wherein the membrane comprises different curvatures in FIGS. 1A and 1B due to the lens shaper acting on the membrane, which curvatures correspond to different focal lengths of the focus variable lens.
Figure 1B:
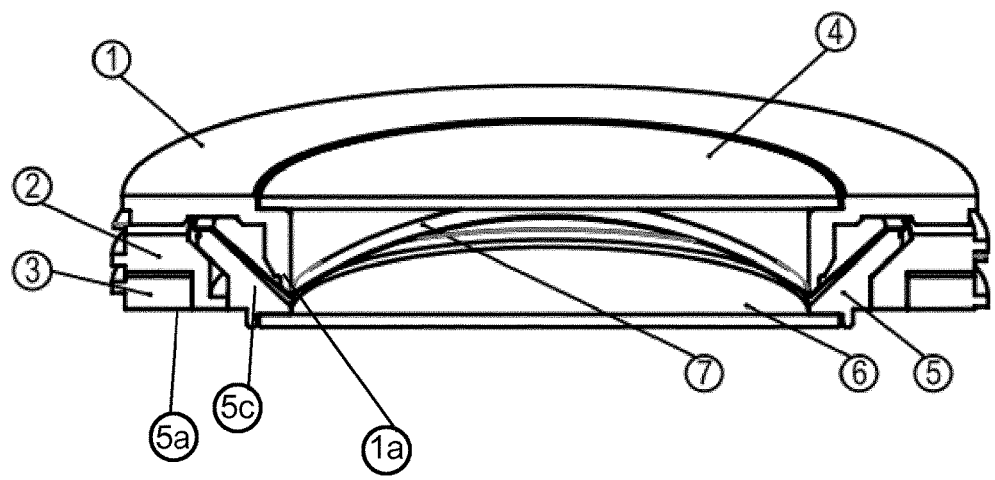
Figure 2:
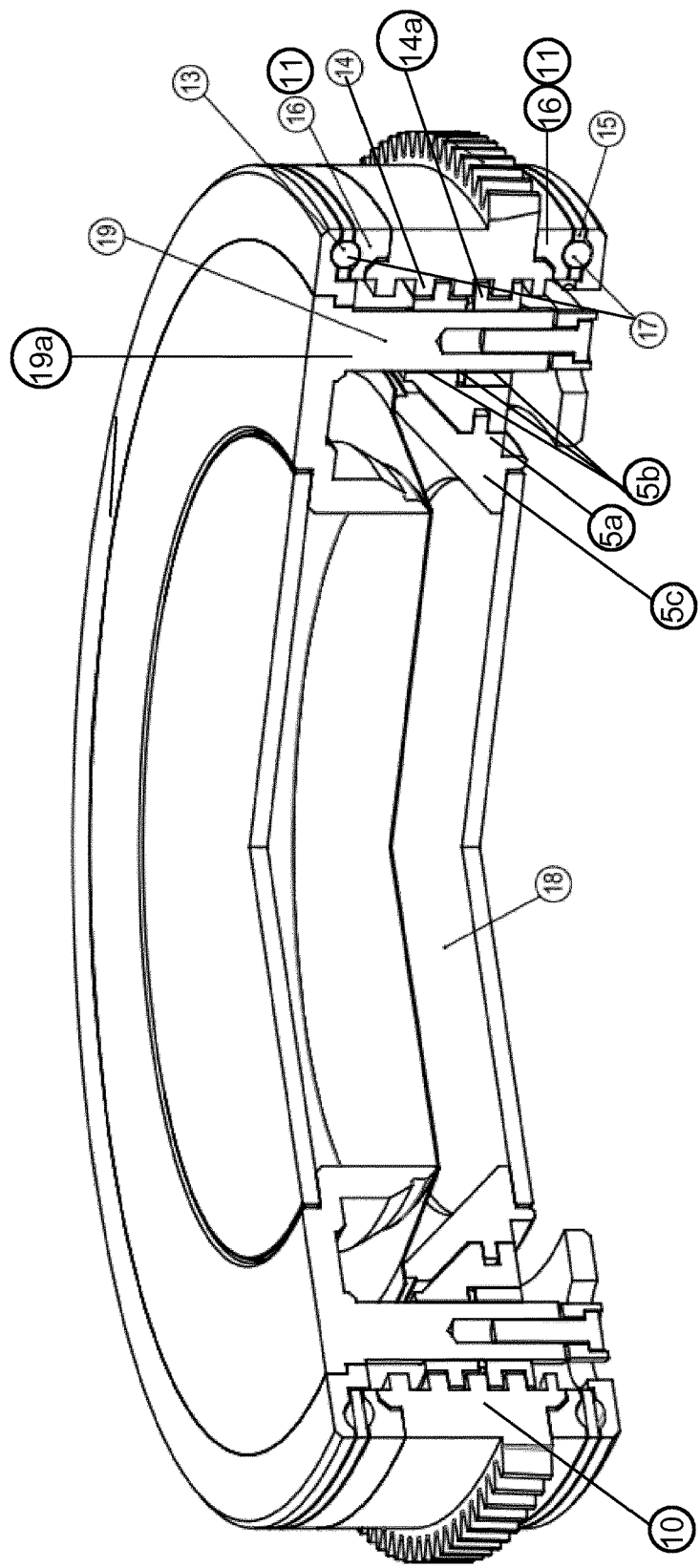
FIG. 2 shows a perspective view of the first embodiment.

Compared to state of the art solutions the improvement and innovation is particularly in the mechanical design which transfers the rotational movement to the linear movement. According to a first and second embodiment, the mechanism is made of at least three main elements: firstly a rotatable thread ring 10 containing a helical thread 14, secondly a fixed element 1 which typically is in mechanical connection to an outer system or housing and contains a preferably circumferential lens-shaping element (also denoted as lens shaper) 1*a* which during tuning is applying force on a part of a central lens container element 5, preferably on an elastically deformable optical element 7, preferably on a transparent elastically deformable membrane 7, and thirdly the inner lens container element 5 itself, containing the inner counterpart 2 of the helical thread 14 of the thread ring 10.

The fixed element 1 can act as rotational guidance for the outer thread ring 10 and at the same time can act as linear guidance for the inner lens container element 5.

Figure 3:
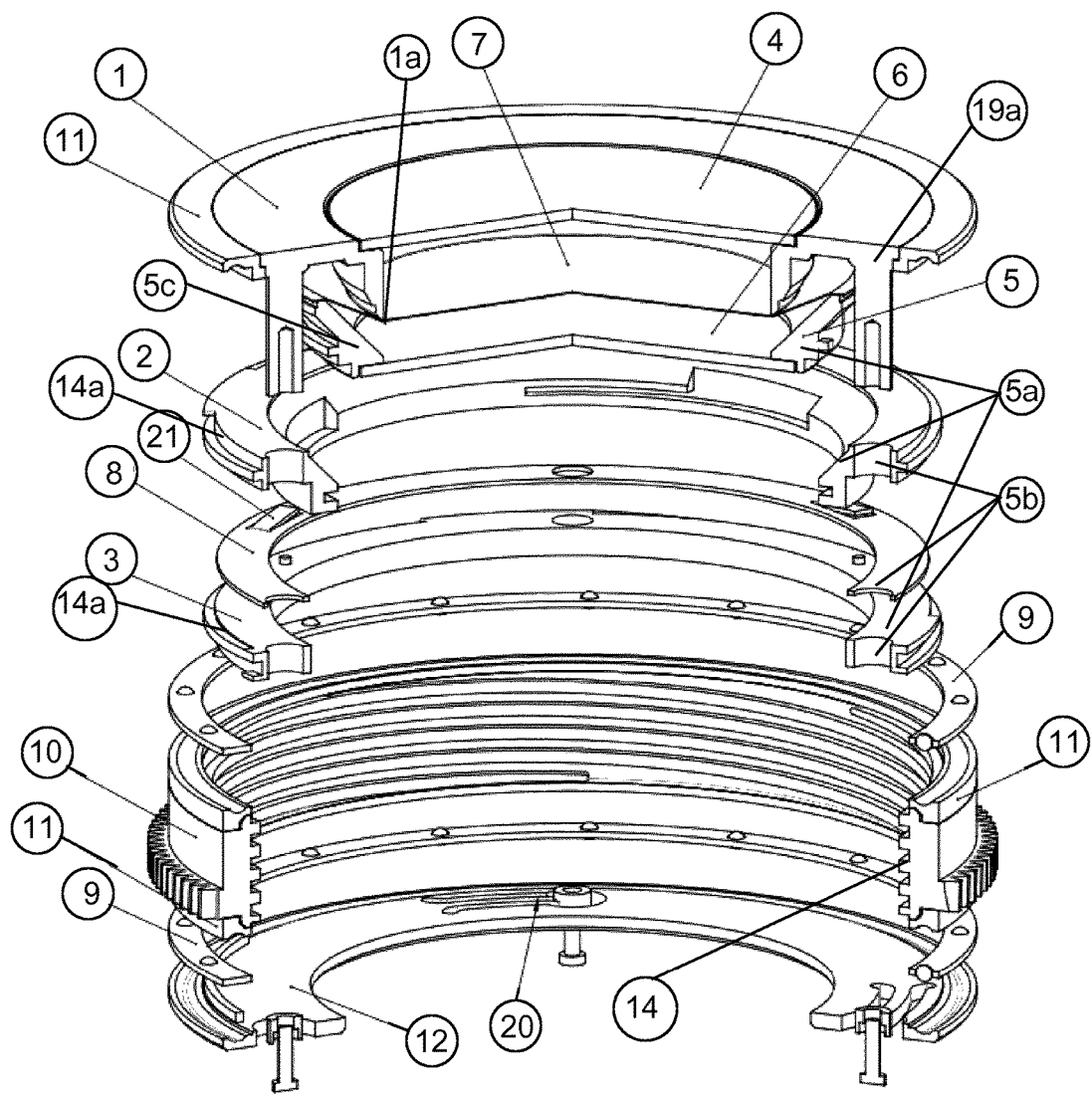
FIG. 3 shows an exploded view of the first embodiment.
Figure 4A:
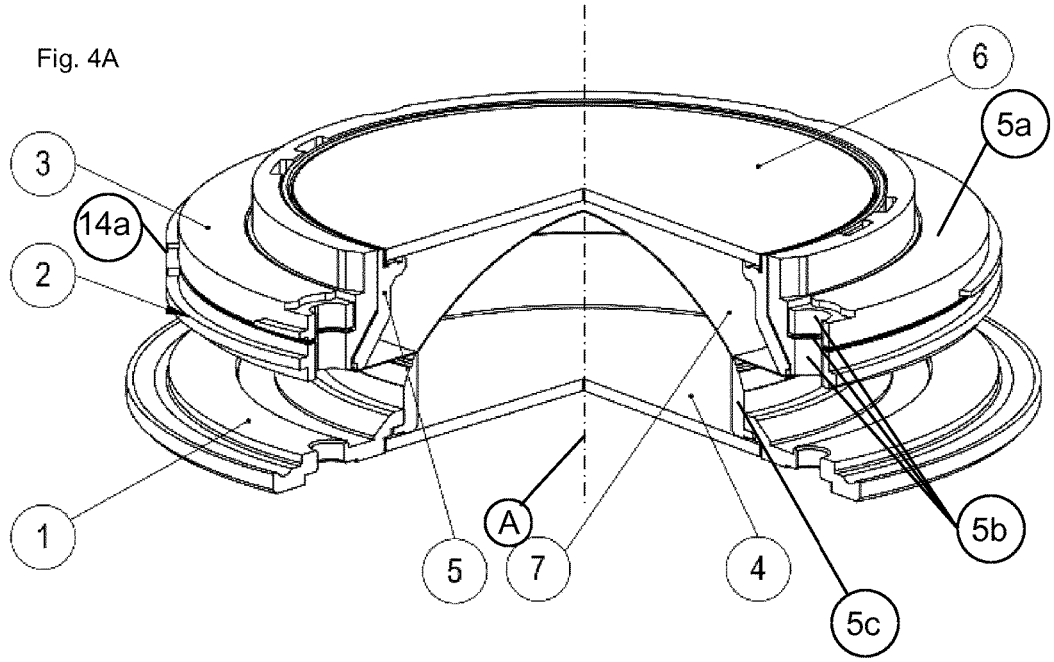
FIG. 4A, 4B show cross sectional views of a container and fixed element of a second embodiment of the lens according to the invention, wherein the membrane comprises different curvatures in FIGS. 4A and 4B due to the lens shaper acting on the membrane, which different curvatures correspond to different focal lengths of the focus variable lens.
Figure 4B:
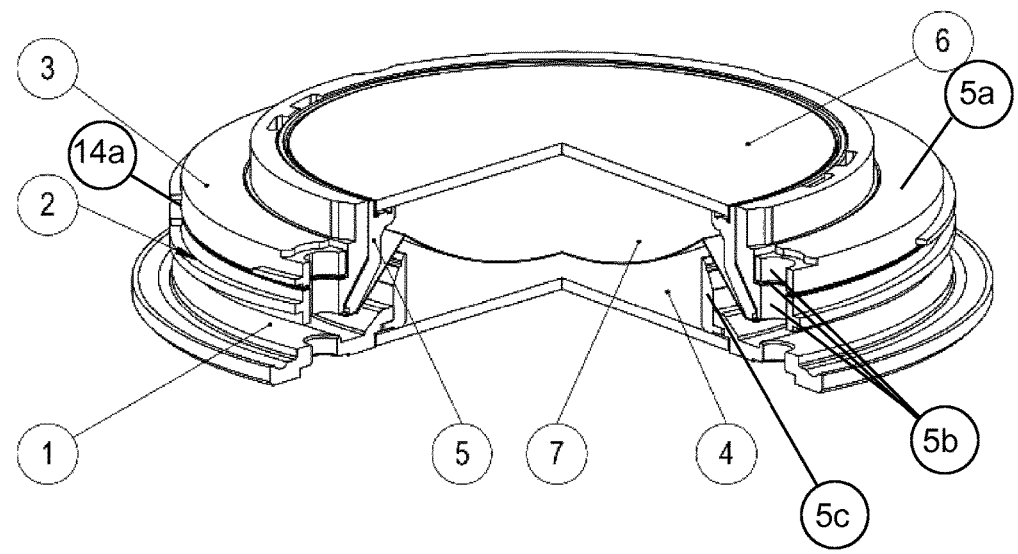
Figure 6:
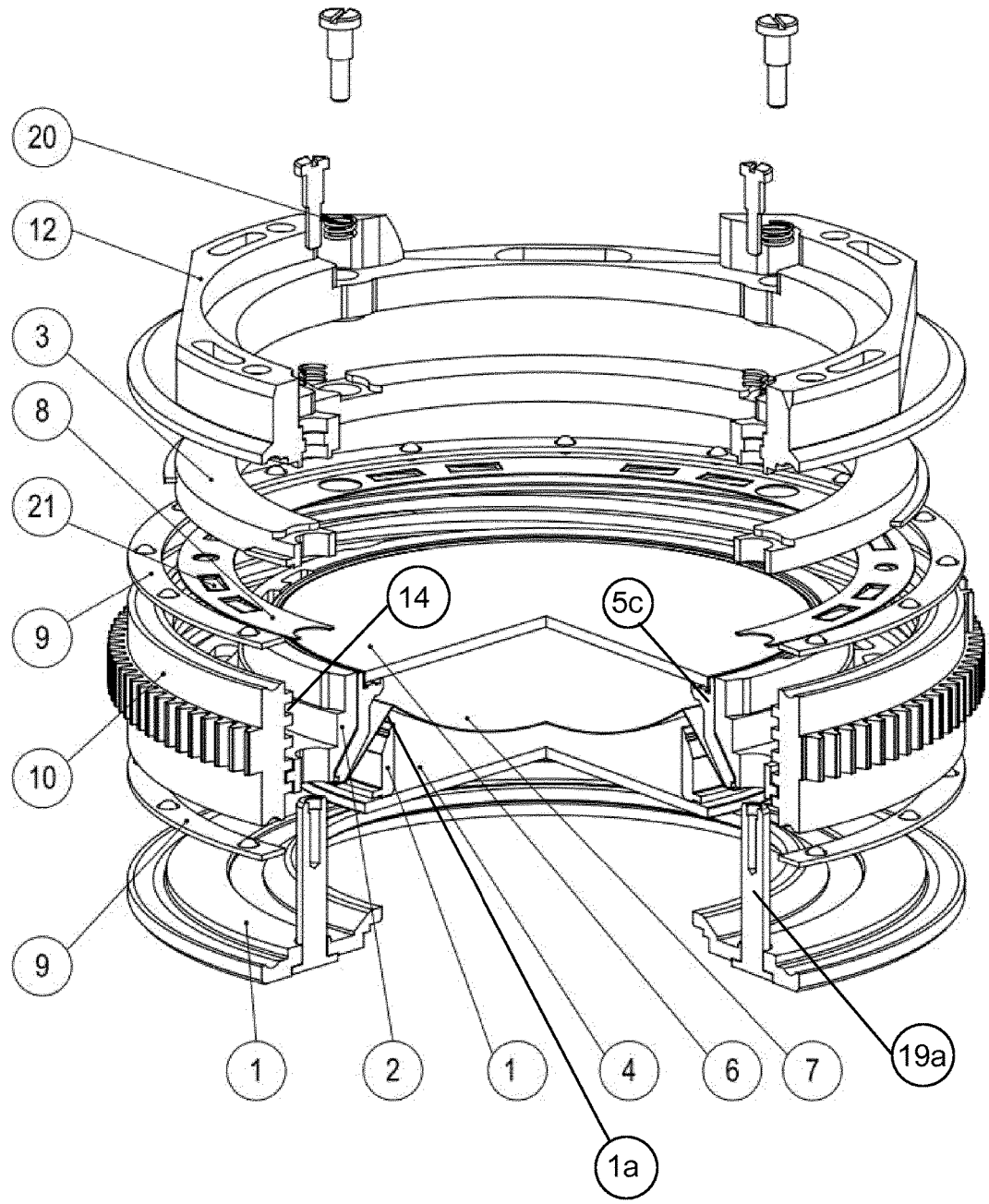
FIG. 6 shows an exploded view of the second embodiment.

Depending on the requirements (such as thermal conductivity, mechanical stiffness, weight, friction coefficient . . . ) that fixed element 1 can be made out of different materials, such as typically aluminum, steel, brass, plastics or other materials. For assembly reasons, the fixed element 1 is typically made out of two or more components, where one or more can be part of a larger system, such as a camera or other optic devices. The fixed element 1 can be designed in a way that the interfaces to the thread ring 10 or to the inner lens container element 5 are created as components for rotational 15 or linear guidance 19 which reduce or adjust mechanical play. To reduce the mechanical friction, both guidances can contain an optimized bearing system. The bearing can be sliding type or ball bearing type 9, 11, 12, 13, 15, 16, 17, while the ball bearing type is preferred to reduce the friction to an absolute minimum. To reach a minimum of mechanical play, the fixed element 1 can contain elastic elements such as helical tension springs 20 (cf. FIG. 6) or at least partially can be designed in a semi-flexible manner as flexure bearing 20 (cf. FIG. 3), such that there is a defined force which keeps the individual parts of the mechanism always in contact. Such flexure bearing element 20 is preferably designed in a way that there is a higher stiffness in radial direction and a lower stiffness in axial direction A (the radial direction runs perpendicular to the axial direction A). For withstanding all directions of force—namely radial and axial type, at least one of such ball bearings is designed as an angular ball bearing 13.

The rotatable thread ring 10 at the interface to the fixed element 1 contains the counterparts of the mentioned bearing (sliding type or ball bearing type) 16, which are also denoted as inner bearings 16 and may be formed as ball track inserts 11 (see below). Central part of the respective bearing 13, 15 preferably is a ball cage 9 and the balls 17 themselves. The balls 17 can be made out of all type of materials, such as steel, ceramic, glass or others. The number and size of balls/spheres 17 is typically a function of the mechanical load, the design and the cost requirements. The spheres 17 are held in place by the ball cage 9 which can be made of different materials, such as plastics, brass or others. For optimized functions or performance, the thread ring 10 can be made out of different components or sections having different properties and functionalities. For example: for a higher mechanical load, an optimized metallic ring 11 (e.g. said ball track insert 11) can be placed at the interface to the bearing cage 9. The thread ring 10 can be combined with a gear of any type to allow a compact transfer of tangential force or momentum. The thread ring 10 can also contain magnets, in a way that it directly acts as the rotor of an electric motor such as a torque motor, or for angular encoding. It can also be combined with optical encoder wheels. The thread ring 10 also contains the helical thread 14 which can be metric, trapezoid, rounded or also other type of thread. The interface to the lens container elements 5 transfers force and therefore typically also can be optimized to reduce mechanical friction. In case of sliding bearing the materials can be chosen accordingly to reduce friction, such as Nycast, NylOil or Delrin, Torlon, Rulon or other plastics, or an appropriate grease could be used. For special applications, the interface can be designed in ball screw system.

The lens container 5 typically consists of a container ring 5*a* that particularly forms or comprises a circumferential lateral wall 5*c*, an elastic membrane 7, a liquid optical body 18 and a typically rigid transparent cover element 6. The liquid optical body may be formed by filling the volume of the container 5 which is delimited by the membrane 7, the container ring 5*a* (particularly said lateral wall 5*c*) and the cover element 6 with a transparent liquid 18. Particularly said membrane 7 and cover element 6 are connected to the lateral wall 5c for forming said volume for the liquid 18. Instead of a liquid also a fluid may be used. Here fluid means liquid or gas or a mixture of a liquid or a gas. Further, particularly, in case of an adaptive mirror, the liquid or fluid does not necessarily have to be transparent.

Preferably, as already indicated above, the container ring 5a is made out of one or more components 2, 3, 5c, 8, where at least one of it, e.g. a first ring or nut 2 which may surround the lateral wall 5c and can be fixed to the lateral wall 5c and which preferably comprises an outer thread 14a that engages with the helical thread 14 is in mechanical contact to the fixed element 1. The interface is acting as axial guidance 19 to allow for precise positioning and block the lens container element 5 from rotation with the thread ring 10. This axial guidance 19 preferably consists out of one or more, but typically three vertical posts 19a which are part of the fixed element 1 and the according through-hole(s) 5b in the lens container ring 5a (e.g. in the first and second ring 2, 3 as well as in the spring element 8). For optimized friction, the materials, the coatings or the lubrication is chosen accordingly. The axial guidance can be arranged in a linear ball bearing design to reduce the friction to a minimum. The interface to the thread ring 10 is particularly optimized in a manner that the system, throughout its complete optical tuning range does not show any kind of mechanical play or hysteresis. This functionality is created by the introduction of one or several elastic elements 8 which introduce a mechanical preload. These elements 8 can either be integrated in the container ring 5a directly by choosing the appropriate elastic material and design, or the container ring 5a can be made out of several components, such as a first (upper) ring or nut 2 and a second (lower) ring or nut 3 with an axial spring element 8 in between, the optical element (e.g. container 5) being particularly only carried by one of it, e.g. by ring 2. The spring 8 is pushing the components 2, 3 apart in a way that the axial contact to the thread ring 10 is maintained always on the same side on the helical thread 14, independent from the lens tuning position. For this, the elastical element/spring 8 may contain an annular flat base being arranged between the two rings 2, 3, wherein the spring 8 comprises portions 21 that protrude from the base in the axial direction and provide a restoring or elastic force when pushed towards the base. Said portions can rest against ring 2 such that the spring tends to push the ring 2 away from ring 3 as described above.

Further, the spring element 8 can be a spiral spring, leaf spring, volute spring, disc spring, azimuth disc spring, elastomer spring, rubber spring or other elements with comparable function. Furthermore, by not only adding an axial load on the spring 8 but also a rotational preload, in particular when using a spiral spring, the mechanical play between the axial guidance 19 and the lower 3 and upper ring 2 can be reduced as both the lower and upper rings 3, 2 are in lateral contact with the axial guidance 19. To further reduce the mechanical friction, it is also possible to add a ball bearing to the helical structure, such as a ball screw system.

Figure 5:
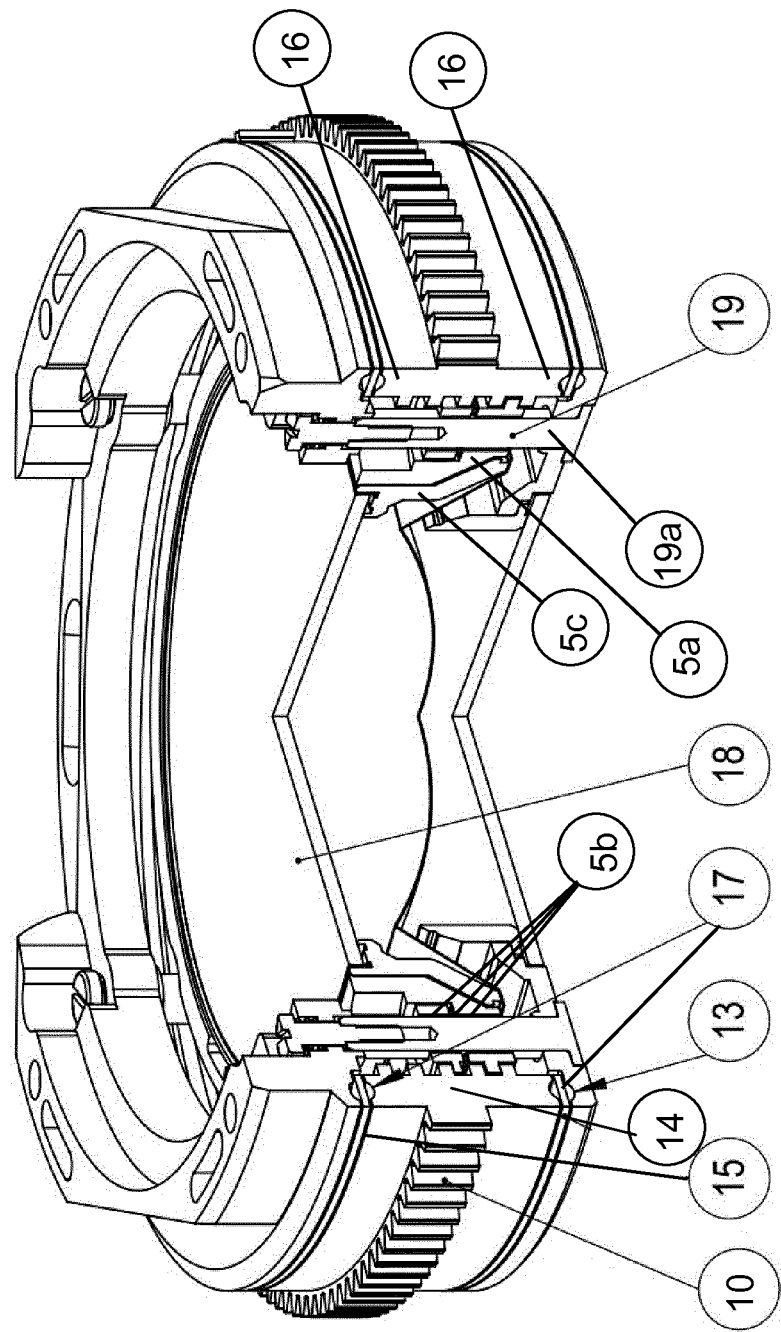
FIG. 5 shows a perspective view of the second embodiment.

Above, the two embodiments have been described in conjunction since they show the same or similar essential components. Particularly, as can be seen from the Figures, the second embodiment may differ from the first one in that the inner bearings 16 (cf. FIG. 5) may be integrally formed with the thread ring 10, while in the first embodiment separate inserts 11 may be used (cf. FIG. 3). Further, the elastic bearing 20 of the second embodiment may be formed as helical tension springs 20 (cf. FIG. 6) while in the first embodiment, a flexure bearing 20 (e.g. flat springs 20) may be used that may be embedded or integrated into housing part 12 (cf. FIG. 3).

REFERENCE NUMERALS USED IN THE DRAWINGS AND SPECIFICATION 1 fixed element comprising lens shaping element (also denoted lens shaper)
1a lens shaping element
2 first ring or nut with outer thread
3 second ring or lock nut with outer thread
4 Top cover glass
5 Container (also denoted container element)
5a Container ring
5b through holes
5c lateral wall
6 Bottom cover glass
7 Membrane
8 Spring structure
9 Ball cage with balls
10 Thread ring with outer helical thread and inner flat thread
11 Ball track insert
12 Housing with ball track and flexure bearing
13 Angular ball bearing
14 Helical thread
14a outer thread of container ring 5a meshing with helical thread 14
15 Ball bearing
16 Inner bearing
17 Balls
18 Liquid
19 Axial guiding interface
20 Flexural bearing or helical tension spring
21 Spring

The invention claimed is:

1. A variable focus lens comprising an elastically deformable optical element (7) and a circumferential mechanism (10, 1, 5, 2, 3, 8, 21) to transfer a rotational movement to an axial movement, wherein by using a ball bearing system (9, 11, 12, 13, 15, 16, 17) the mechanism is optimized in a manner to reduce mechanical friction, friction variation and to improve force-direction dependent positioning insensitivity, wherein the circumferential mechanism comprises an outer thread ring (10) with a helical thread (14), and wherein the lens comprises a container element (5) that is filled with a fluid (18), wherein the container element (5) comprises a container ring (5a), wherein the container ring (5a) comprises an outer thread (14a) that meshes with the helical thread (14) so that the container element (5) is moved axially in an axial direction (A) when the thread ring (10) is rotated about the axial direction (A), and wherein the container ring (5a) comprises a first ring (2) and a second ring (3) which both form said outer thread (14a) of the container ring (5a), wherein a spring element (8) is arranged between the first ring (2) and the second ring (3) and is configured to push said rings (2, 3) apart, so as to reduce an axial play of the helical thread (14).

2. The lens of claim 1, wherein the lens comprises an elastic element (8, 21) to preload the ball bearing system.

3. The lens of claim 1, wherein the lens comprises at least one ring-shaped elastic spring element (8, 21) applying a preloading force in a primarily axial direction (A), avoiding axial play within a helical thread, minimizing optical hysteresis in a focal length thereof.

4. The lens of claim 1, wherein the spring element (8, 21) is also applying a preload in a rotational direction to reduce rotational play.

5. The lens of claim 1, wherein the thread ring (10) is supported on a fixed element (1) via a ball bearing (13) comprised by the ball bearing system so that the thread ring (10) is rotatable with respect to the fixed element (1) about the axial direction (A).

6. The lens of claim 1, wherein the lens comprises a transparent and elastically deformable membrane (7), and a transparent cover element (6) facing said membrane (7) in the axial direction (A), wherein the membrane (7), the container ring (5a) and the cover element (6) delimit a volume of the container element (5) that is filled with the fluid, particularly a transparent liquid (18).

7. The lens of claim 6, wherein the container element (5) is guided by a plurality of posts (19a) protruding from the fixed element (1) in the axial direction (A) and extending through through-holes (5b) in the container ring (5a).

8. The lens of claim 6, wherein a lens shaping element (1a) that protrudes from the fixed element (1) is configured to press against the membrane (7) depending on the axial position of the container element (5) so that a curvature of the membrane (7) and therewith the focal length of the lens is adjustable by said axial movement of the container element (5).

9. The lens according to claim 8, wherein the spring element (8) is configured to push said rings (2, 3) apart in a way that the axial contact to the thread ring (10) is maintained always on the same side on the helical thread (14).

10. The lens of claim 5, wherein the thread ring (10) is also supported on a housing part (12) that faces the fixed element (1) in the axial direction (A) via a further ball bearing (15) comprised by said ball bearing system, wherein said housing part (12) particularly holds a further transparent cover element (4) facing said cover element (6) of the container element (5) in the axial direction (A), and wherein particularly said housing part (12) is connected to the vertical posts (19a) via an elastic bearing (20).

11. A variable focus lens comprising an elastically deformable optical element (7) and a circumferential mechanism (10, 1, 5, 2, 3, 8, 21) to transfer a rotational movement to an axial movement, wherein by using a ball bearing system (9, 11, 12, 13, 15, 16, 17) the mechanism is optimized in a manner to reduce mechanical friction, friction variation and to improve force-direction dependent positioning insensitivity, wherein the lens comprises a container element that is filled with a fluid, wherein the container element (5) comprises a container ring (5a), wherein the container element (5) is guided by a plurality of posts (19a) extending through through-holes (5b) in the container ring (5a).

12. A variable focus lens comprising an elastically deformable optical element (7) and a circumferential mechanism (10, 1, 5, 2, 3, 8, 21) to transfer a rotational movement to an axial movement, wherein by using a ball bearing system (9, 11, 12, 13, 15, 16, 17) the mechanism is optimized in a manner to reduce mechanical friction, friction variation and to improve force-direction dependent positioning insensitivity, wherein the circumferential mechanism comprises an outer thread ring (10) with a helical thread (14), which thread ring (10) is supported on a fixed element (1) via a ball bearing (13) comprised by the ball bearing system so that the thread ring (10) is rotatable with respect to the fixed element (1) about an axial direction (A), and wherein the thread ring (10) is also supported on a housing part (12) that faces the fixed element (1) in the axial direction (A) via a further ball bearing (15) comprised by said ball bearing system.

\* \* \* \* \*